(12) United States Patent
Bratkovski et al.

(10) Patent No.: US 7,292,334 B1
(45) Date of Patent: *Nov. 6, 2007

(54) BINARY ARRAYS OF NANOPARTICLES FOR NANO-ENHANCED RAMAN SCATTERING MOLECULAR SENSORS

(75) Inventors: Alexandre M. Bratkovski, Mountain View, CA (US); Theodore I. Kamins, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 226 days.

This patent is subject to a terminal disclaimer.

(21) Appl. No.: 11/090,352

(22) Filed: Mar. 25, 2005

(51) Int. Cl.
G01J 3/44 (2006.01)
(52) U.S. Cl. .................................... 356/301
(58) Field of Classification Search ............... 356/301, 356/326; 977/701, 707, 773
See application file for complete search history.

(56) References Cited

U.S. PATENT DOCUMENTS

| | | | |
|---|---|---|---|
| 4,674,878 A | 6/1987 | Vo-Dinh | |
| 4,944,985 A | 7/1990 | Alexander et al. | |
| 5,017,007 A | 5/1991 | Milne et al. | |
| 5,242,828 A | 9/1993 | Bergstrom et al. | |
| 5,255,067 A | 10/1993 | Carrabba et al. | |
| 5,527,712 A * | 6/1996 | Sheehy | 436/525 |
| 5,609,907 A | 3/1997 | Natan | |
| 5,772,905 A | 6/1998 | Chou | |
| 5,837,552 A | 11/1998 | Cotton et al. | |
| 5,864,397 A * | 1/1999 | Vo-Dinh | 356/301 |
| 5,885,753 A | 3/1999 | Crooks et al. | |
| 6,025,202 A | 2/2000 | Natan | |
| 6,149,868 A * | 11/2000 | Natan et al. | 422/82.05 |
| 6,165,911 A | 12/2000 | Calveley | |
| 6,242,264 B1 | 6/2001 | Natan et al. | |
| 6,248,674 B1 | 6/2001 | Kamins et al. | |
| 6,365,059 B1 | 4/2002 | Pechenik | |
| 6,406,777 B1 | 6/2002 | Boss et al. | |
| 6,432,740 B1 | 8/2002 | Chen | |

(Continued)

FOREIGN PATENT DOCUMENTS

WO WO 98/10289 A1 3/1998

(Continued)

OTHER PUBLICATIONS

Wei et al., "Engineering 'Hot Spots' for Surface Enhanced Raman Scattering", Proceedings of SPIE vol. 5221 Plasmonics: Metallic Nanostructures and Their Optical Properties, pp. 92-98, (2003).*

(Continued)

Primary Examiner—Tarifur Chowdhury
Assistant Examiner—Jonathan M Hansen (57) ABSTRACT

A nano-enhanced Raman scattering (NERS)-active structure includes a substrate, a monolayer of nanoparticles disposed on a surface of the substrate, and a spacer material surrounding each nanoparticle in the monolayer of nanoparticles. The monolayer of nanoparticles includes a first plurality of nanoparticles and a second plurality of nanoparticles. The nanoparticles of the second plurality are interspersed among the first plurality and exhibit a plasmon frequency that differs from any plasmon frequency exhibited by the first plurality. Also described are a method for forming such a NERS-active structure and a NERS system that includes a NERS-active structure, an excitation radiation source, and a detector for detecting Raman scattered radiation.

50 Claims, 4 Drawing Sheets

U.S. PATENT DOCUMENTS

| | | | |
|---|---|---|---|
| 6,579,721 | B1 | 6/2003 | Natan et al. |
| 6,623,977 | B1 | 9/2003 | Farquharson et al. |
| 6,649,683 | B2 | 11/2003 | Bell |
| 6,773,616 | B1 | 8/2004 | Chen et al. |
| 6,778,316 | B2* | 8/2004 | Halas et al. ............. 359/296 |
| 6,781,690 | B2* | 8/2004 | Armstrong et al. ........ 356/301 |
| 7,057,732 | B2* | 6/2006 | Jorgenson et al. ......... 356/445 |
| 7,212,284 | B2* | 5/2007 | Deng et al. ............. 356/301 |
| 2002/0142480 | A1 | 10/2002 | Natan |
| 2003/0059820 | A1* | 3/2003 | Vo-Dinh ................. 435/6 |
| 2003/0120137 | A1 | 6/2003 | Pawluczyk |
| 2003/0157732 | A1 | 8/2003 | Baker et al. |
| 2003/0165418 | A1 | 9/2003 | Ajayan et al. |
| 2003/0174384 | A1* | 9/2003 | Halas et al. ............. 359/296 |
| 2003/0231304 | A1 | 12/2003 | Chan et al. |
| 2004/0077844 | A1 | 4/2004 | Jacobson et al. |
| 2004/0134778 | A1 | 7/2004 | Stelzle et al. |
| 2004/0135997 | A1* | 7/2004 | Chan et al. ............. 356/301 |
| 2004/0150818 | A1* | 8/2004 | Armstrong et al. ........ 356/301 |
| 2005/0142567 | A1* | 6/2005 | Su et al. ................. 435/6 |
| 2006/0017918 | A1* | 1/2006 | Cullum et al. ............. 356/301 |
| 2006/0054881 | A1* | 3/2006 | Li et al. ................. 257/19 |
| 2006/0164634 | A1* | 7/2006 | Kamins et al. ............. 356/301 |
| 2006/0209300 | A1* | 9/2006 | Kamins et al. ............. 356/301 |

FOREIGN PATENT DOCUMENTS

WO    WO 2004/059279 A2    7/2004

OTHER PUBLICATIONS

Collier, C.P., et al., "Reversible Tuning of Silver Quantum Dot Monolayers Through the Metal-Insulator Transition," Science, vol. 277, pp. 1978-1981, Sep. 26, 1997.

Drew, Christopher, et al., "Metal Oxide-Coated Polymer Nanofibers," Nano Lett., vol. 3, No. 2, pp. 143-147, 2003.

Garcia, F.J., et al., "Collective Theory for Surface Enhanced Raman Scattering," Physical Review Letters, vol. 77, No. 6, pp. 1163-1166, Aug. 5, 1996.

Green, Mino, et al., "SERS Substrates Fabricated by Island Lithography: The Silver/Pyridine System," J. Phys. Chem. B, vol. 107, No. 47, pp. 13015-13021, 2003.

Kamins, T.I., et al., "Chemically vapor deposited Si nanowires nucleated by self-assembled Ti islands on patterned and unpatterned Si substrates," Physica E 13, pp. 995-998, 2002.

Kneipp, Katrin, et al., "Single Molecule Detection Using Surface-Enhanced Raman Scattering (SERS)," Physical Review Letters, vol. 78, No. 9, pp. 1667-1670, Mar. 3, 1997.

Liu, Feng-Ming, et al., "Efficient SERS substrates made by electroless silver deposition into patterned silicon structures," J. Mater. Chem., 14, pp. 1526-1532, 2004.

Nie, Shuming, et al., "Probing Single Molecules and Single Nanoparticles by Surface-Enhanced Raman Scattering," Science, vol. 275, pp. 1102-1106, Feb. 21, 1997.

Otto, Andreas, "Some Aspects of the Mechanisms of SERS," Heinrich-Heine Universitat Dusseldorf, Lehrstuhl fur Oberflachenwissenschaft, Universitatsstr. 1, 40225 Dusseldorf, F.R. Germany, EU, e-mail: ott@rz.uni-duesseldorf.dc, 4 pages.

Otto, Andreas, "What is observed in single molecule SERS?," submitted to J. Raman Spectroscopy, Lehrstuhl fur Oberflachenwissenschaft, Heinrich-Heine-Universitat Dusseldorf, D 40225 Dusseldorf, FR Germany, EU, 4 pages.

Pinto, N.J., et al., "Electroless Deposition of Thin Metallic Films on Polymer Fibers Prepared via Electrospinning," Polymer Preprints, 44(2), pp. 138-139, 2003.

Whang, Dongmok, et al., "Nanolithography Using Hierarchically Assembled Nanowire Masks," Nano Lett. vol. 3, No. 7, pp. 951-954, 2003.

* cited by examiner

BINARY ARRAYS OF NANOPARTICLES FOR NANO-ENHANCED RAMAN SCATTERING MOLECULAR SENSORS

CROSS-REFERENCE TO RELATED APPLICATION

The present invention is related to an invention disclosed in an application filed Mar. 17, 2005 by Kamins et al. entitled AN ORDERED ARRAY OF NANOPARTICLES FOR EFFICIENT NANOENHANCED RAMAN SCATTERING DETECTION AND METHODS OF FORMING THE SAME.

FIELD OF THE INVENTION

The present invention relates to nano-enhanced Raman spectroscopy (NERS). More particularly, the invention relates to NERS-active structures for use as analyte substrates in NERS, methods for forming NERS-active structures, NERS systems, and methods for performing NERS using NERS-active structures.

BACKGROUND OF THE INVENTION

Raman spectroscopy is a well-known technique for analyzing molecules or materials. In conventional Raman spectroscopy, high intensity monochromatic radiation provided by a radiation source, such as a laser, is directed onto an analyte (or sample) that is to be analyzed. A majority of the photons of the incident radiation are elastically scattered by the analyte. In other words, the scattered photons have the same energy, and thus the same wavelength, as the incident photons. However, a very small fraction of the photons, typically about 1 in $10^7$, are inelastically scattered by the analyte. These inelastically scattered photons have a different wavelength than the incident photons. This inelastic scattering of photons is termed "Raman scattering." The Raman scattered photons can have wavelengths less than, or, more typically, greater than the wavelength of the incident photons.

When an incident photon collides with the analyte, energy can be transferred from the photon to the molecules or atoms of the analyte, or from the molecules or atoms of the analyte to the photon. When energy is transferred from the incident photon to the analyte, the Raman scattered photon will have a lower energy and a corresponding longer wavelength than the incident photon. These Raman scattered photons having lower energy than the incident photons are collectively referred to in Raman spectroscopy as the "Stokes radiation." A small fraction of the analyte molecules or atoms can be in an energetically excited state when photons are incident thereon. When energy is transferred from the analyte to the incident photon, the Raman scattered photon will have a higher energy and a corresponding shorter wavelength than the incident photon. These Raman scattered photons having higher energy than the incident photons are commonly referred to in Raman spectroscopy as the "anti-Stokes radiation." The Stokes radiation and the anti-Stokes radiation collectively are referred to as the Raman scattered radiation or the Raman signal.

The Raman scattered radiation is detected by a detector that typically includes a wavelength-dispersive spectrometer and a photomultiplier for converting the energy of the impinging photons into an electrical signal. The characteristics of the electrical signal are at least partially a function of both the energy of the Raman scattered photons as evidenced by their wavelength, frequency, or wave number, and the number of the Raman scattered photons as evidenced by the intensity of the Raman scattered radiation. The electrical signal generated by the detector can be used to produce a spectral graph illustrating the intensity of the Raman scattered radiation as a function of the wavelength of the Raman scattered radiation. Analyte molecules and materials generate unique Raman spectral graphs. The unique Raman spectral graph obtained by performing Raman spectroscopy can be used for many purposes including identification of an unknown analyte or determination of physical and chemical characteristics of a known analyte.

Raman scattering of photons is a weak process. As a result, powerful, costly laser sources typically are used to generate high intensity incident radiation to increase the intensity of the weak Raman scattered radiation for detection. Surface-enhanced Raman spectroscopy (SERS) is a technique that allows for enhancement of the intensity of the Raman scattered radiation relative to conventional Raman scattering. In SERS, the analyte molecules typically are adsorbed onto or placed adjacent to a metal surface or structure. Interactions between the analyte and the metal structure cause an increase in the intensity of the Raman scattered radiation. The mechanism by which the intensity of the Raman scattered radiation is enhanced is not completely understood. Two main theories of enhancement mechanisms have been presented in the literature: electromagnetic enhancement and chemical enhancement. For further discussion of these enhancement mechanism theories, see A. M. Michaels, M. Nirmal, & L. E. Brus, "Surface Enhanced Raman Spectroscopy of Individual Rhodamine 6G Molecules on Large Ag Nanocrystals," *J. Am. Chem. Soc.* 121, 9932-39 (1999).

Several types of metallic structures have been employed in SERS techniques to enhance the intensity of Raman scattered radiation that is scattered by analyte molecules adjacent thereto. Some examples of such structures include electrodes in electrolytic cells, metal colloid solutions, and metal substrates, such as a roughened metal surface or metal "islands" formed on a substrate. For example, it has been shown that adsorbing analyte molecules onto or near a specially roughened metal surface made from gold or silver can enhance the effective Raman scattering intensity by factors of between $10^3$ and $10^6$, when averaged over the illuminated area of the sample.

Recently, SERS has been performed employing randomly oriented nanometer-scale metallic needles and particles, as opposed to a simple roughened metallic surface. This process will be referred to hereinafter as nano-enhanced Raman spectroscopy (NERS). The intensity of the Raman scattered photons from a molecule adsorbed on such a metal surface can be increased by factors as high as $10^{16}$. At this level of sensitivity, NERS has been used to detect single molecules. Detecting single molecules with high sensitivity and molecular specificity is of great interest in the fields of chemistry, biology, medicine, pharmacology, and environmental science. However, it is unknown what configurations, including size, shape and spacing, of metallic particles will enhance the intensity of Raman scattered radiation most effectively.

Accordingly, there is a need for NERS substrates that include metallic particles, the size, separation, and local configuration of which can be controlled to optimize the enhancement of the intensity of Raman scattered radiation by the NERS analyte substrate.

BRIEF SUMMARY OF THE INVENTION

In one aspect, the present invention includes a two-dimensional array of nanoparticles usable for enhancing Raman scattered radiation in NERS. The array of nanoparticles includes a first plurality of nanoparticles and a second plurality of nanoparticles. The second plurality of nanoparticles have a size and shape substantially similar to the size and shape of the first plurality of nanoparticles. The second plurality of nanoparticles exhibits a plasmon frequency that differs from any plasmon frequency exhibited by the first plurality of nanoparticles. The nanoparticles of the second plurality of nanoparticles are interspersed among the nanoparticles of the first plurality of nanoparticles in the two-dimensional array of nanoparticles.

In another aspect, the present invention includes a monolayer of nanoparticles for use as a NERS-active structure. The monolayer of nanoparticles includes a first plurality of nanoparticles and a second plurality of nanoparticles. The second plurality of nanoparticles is interspersed among the first plurality of nanoparticles. The second plurality of nanoparticles exhibits a plasmon frequency that differs from any plasmon frequency that is exhibited by the first plurality of nanoparticles, if any. The concentration of the second plurality of nanoparticles in the monolayer of nanoparticles is below or near a percolation threshold.

In another aspect, the present invention includes a NERS-active structure that includes a substrate, a monolayer of nanoparticles disposed on a surface of the substrate, and a spacer material partially surrounding each nanoparticle in the monolayer of nanoparticles. The monolayer of nanoparticles includes a first plurality of nanoparticles and a second plurality of nanoparticles. The second plurality of nanoparticles is interspersed among the first plurality of nanoparticles. The second plurality of nanoparticles exhibits a plasmon frequency that differs from any plasmon frequency that is exhibited by the first plurality of nanoparticles, if any. The concentration of the second plurality of nanoparticles in the monolayer of nanoparticles is below or near a percolation threshold. The spacer material separates each nanoparticle from adjacent nanoparticles by a selected distance. The spacer material covers less than the entire surface area of each nanoparticle.

In yet another aspect, the present invention includes a NERS system that includes such a NERS-active structure. The NERS system further includes an excitation radiation source configured to irradiate the NERS-active structure and a detector configured to receive Raman scattered radiation scattered by an analyte located adjacent to the NERS-active structure.

In another aspect, the present invention includes a method for forming a NERS-active structure. The method includes providing a mixture of nanoparticles including a first plurality of nanoparticles of a first material and a second plurality of nanoparticles of a second material. The concentration of the second plurality of nanoparticles in the mixture is less than the concentration of the first plurality of nanoparticles. The second plurality of nanoparticles exhibits a plasmon frequency that differs from any plasmon frequency that is exhibited by the first plurality of nanoparticles, if any. Each nanoparticle in the mixture of nanoparticles is coated with a spacer material. A monolayer of the nanoparticles is formed on a surface of a fluid and the monolayer is transferred from the surface of the fluid to a surface of the substrate by placing the substrate in contact with the monolayer of nanoparticles on the surface of the fluid. At least a portion of the spacer material is removed.

The features, advantages, and alternative aspects of the present invention will be apparent to those skilled in the art from a consideration of the following detailed description taken in combination with the accompanying drawings.

BRIEF DESCRIPTION OF THE DRAWINGS

While the specification concludes with claims particularly pointing out and distinctly claiming that which is regarded as the present invention, the advantages of this invention can be more readily ascertained from the following description of the invention when read in conjunction with the accompanying drawings in which:

DETAILED DESCRIPTION OF THE INVENTION

The present invention relates to nano-enhanced Raman spectroscopy (NERS). More particularly, the invention relates to NERS-active structures for use as analyte substrates in NERS, methods for forming NERS-active structures, NERS systems, and methods for performing NERS using NERS-active structures.

The term "analyte" as used herein means any molecule, molecules, material, substance, or matter that is to be analyzed by NERS.

The term "NERS-active structure" as used herein means a structure that is capable of increasing the number of Raman scattered photons that are scattered by an analyte when the analyte is located adjacent to the structure and the analyte and structure are subjected to electromagnetic radiation.

The term "NERS-active material" as used herein means a material that, when formed into appropriate geometries or configurations, is capable of increasing the number of Raman scattered photons that are scattered by an analyte when the analyte is located adjacent the material, and the analyte and material are subjected to electromagnetic radiation. NERS-active materials can be used to form NERS-active structures.

The term "nanoparticle" as used herein means a particle having cross-sectional dimensions of less than about 100 nanometers. Examples of nanoparticles include, but are not limited to, nanodots, nanowires, nanocolumns, and nanospheres.

The term "percolation threshold" as used herein means the critical fraction of nanoparticle sites in an array of possible nanoparticle sites that must be filled with nanoparticles to create a continuous path of adjacent nanoparticles extending from one side of a structure to another when the nanoparticle sites are filled in a random manner.

The term "ligand" as used herein means an atom, molecule, ion or functional group that may be attached to one or more nanoparticles or to a substrate.

The term "polymerize" as used herein means to form a generally solid structure from a liquid or gel by forming bonds between individual molecules in the liquid or gel. The term "polymerize" as used herein includes, for example, the formation of a network structure by forming cross-linking bonds between individual molecules, the formation of long, repeating polymer chains from small monomeric units or mers, and the formation of cross-linking bonds between long, repeating polymer chains.

The illustrations presented herein are not meant to be actual views of any particular NERS-active structure, but are merely idealized representations which are employed to describe the present invention. Additionally, elements common between figures retain the same numerical designation.

Figure 1:
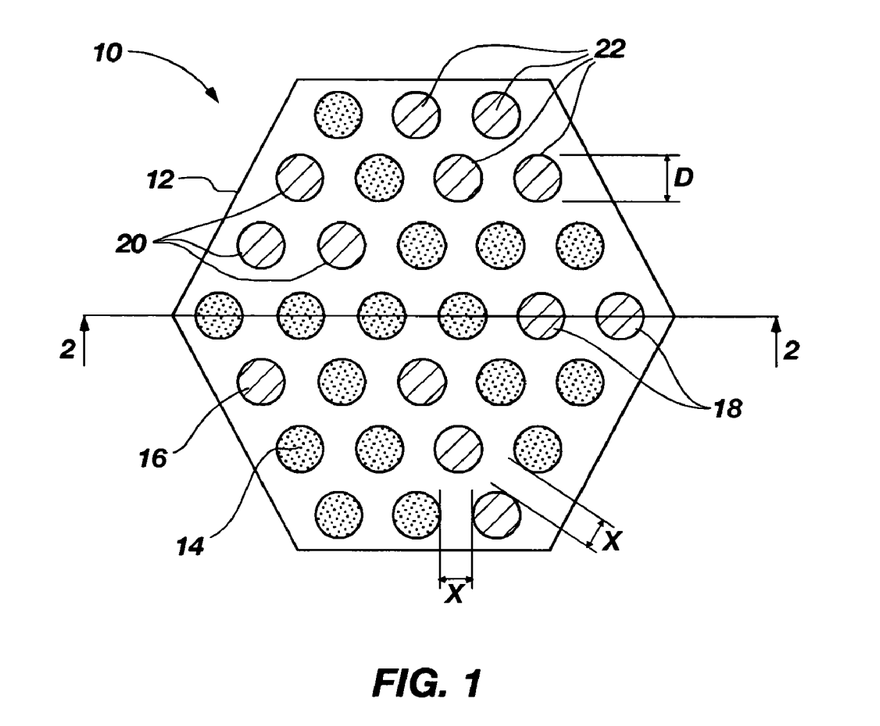
FIG. 1 is top plan view of an exemplary embodiment of a NERS-active structure according to the invention.

FIG. 1 is a top plan view of an exemplary NERS-active structure 10 that embodies teachings of the present invention. The NERS-active structure 10 includes a two-dimensional array of nanoparticles disposed on a surface of a substrate 12. The two-dimensional array of nanoparticles is a binary array that includes a first plurality of inactive nanoparticles 14 and a second plurality of metallic active nanoparticles 16. The first plurality of inactive nanoparticles 14 are shown by shading with dots, while the second plurality of metallic active nanoparticles 16 are shown by shading with cross-hatching. The metallic active nanoparticles 16 are interspersed among the inactive nanoparticles 14. The plurality of inactive nanoparticles 14 also can be metallic. However, the active nanoparticles 16 exhibit a plasmon resonance frequency differing from any plasmon resonance frequency exhibited by the inactive nanoparticles 14 and should not interact in other ways with plasmons from inactive nanoparticles 14.

The nanoparticles 14, 16 can have a generally spherical shape and a diameter D (See FIG. 2) of less than about 100 nanometers. More particularly, the nanoparticles 14, 16 can have a diameter D in a range from about 1 nanometer to about 25 nanometers, or even a range from about 1 nanometer to about 5 nanometers.

The number of metallic active nanoparticles 16 in the two-dimensional array of nanoparticles is below or near the percolation threshold. Because the number of metallic active nanoparticles 16 is below or near the percolation threshold, isolated nanoparticles 16, isolated pairs such as pair 18, isolated triplets such as triplet 20, isolated quadruplets such as quadruplet 22, etc., of metallic active nanoparticles 16 are randomly provided in the two-dimensional array of nanoparticles 14, 16. These structures formed by metallic active nanoparticles 16 may be surrounded by inactive nanoparticles 14 that separate the structures from other structures formed by metallic active nanoparticles 16.

Nanoparticles 14, 16 in the two-dimensional array are separated from adjacent nanoparticles 14, 16 in the two-dimensional array by a distance X. The distance X can be in a range from about 1 nanometer to about 100 nanometers. More particularly, the distance X can be in a range from about 1 nanometer to about 50 nanometers, or even in a range from about 1 nanometer to about 10 nanometers.

Each metallic active nanoparticle 16 can be formed from, for example, gold, silver, copper, or any other NERS-active material. Each inactive nanoparticle 14 can be formed from, for example, cobalt, silica, alumina, or any other material that either does not exhibit a plasmon resonance frequency, that exhibits a plasmon resonance frequency at a frequency differing from the plasmon resonance frequency exhibited by the metallic active nanoparticles 16, or that otherwise does not interact with plasmons from the metallic active nanoparticles. This allows isolated surface plasmon modes to be generated in the regions of the metallic active nanoparticles 16 when the NERS-active structure 10 is subjected to electromagnetic radiation at a particular frequency or frequencies without generating interacting surface plasmon modes in the regions of the inactive nanoparticles 14.

The substrate 12 can be formed from, for example, silicon, silica, zirconia, alumina, tin oxides, perovskite oxides, and selected metals. The material used to form the substrate 12 should not exhibit a plasmon resonance frequency, or should exhibit a plasmon resonance frequency differing from the plasmon resonance frequency exhibited by the active nanoparticles 16. In this configuration, isolated surface plasmon modes may be generated in the regions of the metallic active nanoparticles 16 when the NERS-active structure 10 is subjected to electromagnetic radiation at a particular frequency or frequencies without generating interacting surface plasmon modes in the substrate 12.

Figure 2:
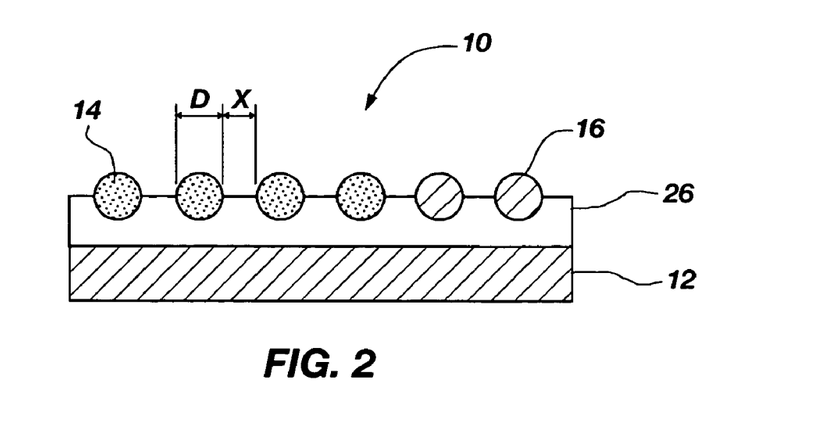
FIG. 2 is a cross-sectional view of the NERS-active structure of FIG. 1 taken along section line 2-2 therein.

FIG. 2 is a cross-sectional view of the NERS-active structure 10 of FIG. 1 taken along section line 2-2 therein. As seen in FIG. 2, the nanoparticles 14, 16 of the two-dimensional array of nanoparticles may be at least partially covered by a spacer material 26 that separates each nanoparticle 14, 16 from adjacent nanoparticles. The spacer material 26 may cover less than the entire surface area of each nanoparticle 14, 16 in the two-dimensional array of nanoparticles 14, 16 to allow an analyte to be adsorbed onto a portion of the surface area of the active nanoparticles 16. The spacer material 26 may cover approximately the lower half of the surface area of each of the nanoparticles 14, 16, leaving the top halves thereof exposed. In one particular embodiment of the invention, the spacer material 26 may include organic ligand molecules. In another embodiment of the invention, the spacer material 26 may include a polymerized material. Furthermore, the spacer material 26 may bind each nanoparticle 14, 16 in the two-dimensional array to the substrate 12, to adjacent nanoparticles 14, 16, or to both the substrate 12 and adjacent nanoparticles 14, 16.

Isolated pairs of nanoparticles 16 such as pair 18, isolated triplets such as triplet 20, and isolated quadruplets such as quadruplet 22 of NERS-active structure 10 shown in FIGS. 1-2 provide regions on the surface of the NERS-active structure 10 that vary in local configuration and allow generation of plasmon modes having different characteristics. The best local configuration of active nanoparticles 16 for enhancing the Raman signal typically differs for different analytes. In addition, the best local configuration of active nanoparticles 16 for a particular analyte typically is not known beforehand. When an analyte is adsorbed on the surface of NERS-active structure 10 and enhanced Raman spectroscopy is performed, the best local configuration of active nanoparticles 16 for enhancing the Raman signal for that particular analyte can be identified by determining which regions on the surface of the NERS-active structure 10 enhance the Raman scattering in the most efficient manner. The intensity of the Raman scattered radiation will be strongest at these regions.

As seen in FIG. 2, the two-dimensional array of nanoparticles 14, 16 of NERS-active structure 10 may form a monolayer of nanoparticles on the surface of the substrate 12.

FIGS. 3-7 illustrate an exemplary method for forming the NERS-active structure 10 shown in FIGS. 1-2 that incorporates teachings of the present invention. The method can include use of Langmuir-Blodgett type techniques and Langmuir-Schaefer type techniques to form the monolayer of nanoparticles 14, 16 on the surface of the substrate 12.

Commercially available inactive nanoparticles 14 and metallic active nanoparticles 16 can be provided, and mixed together to form a mixture of nanoparticles. The concentration of metallic active nanoparticles 16 can be sufficiently less than the concentration of inactive nanoparticles 14 in the mixture, such that when the mixture of nanoparticles 14, 16 forms a two-dimensional monolayer array of nanoparticles, the concentration of metallic active nanoparticles 16 in the two-dimensional array is below or near the percolation threshold.

Figure 3:
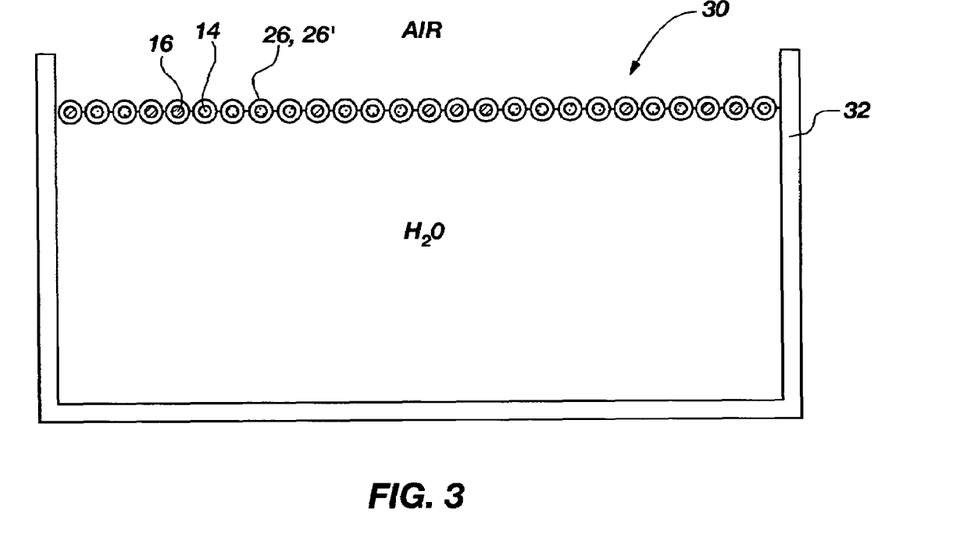
FIGS. 3-7 illustrate an exemplary method for forming the NERS-active structure of FIGS. 1-2.

As shown in FIG. 3, the nanoparticles 14, 16 may be coated with the spacer material 26 or with precursor material 26' that will be used to form the spacer material 26 and provided on the surface of a fluid to form a Langmuir film. For example, the nanoparticles 14, 16 may be coated with organic ligand molecules that include a hydrophobic portion, a first functional group, and a second functional group. The hydrophobic portion may include, for example, an elongated alkyl chain. The first functional group may be used to attach the molecules of the spacer material 26 or precursor materials 26' to the nanoparticles 14, 16 and may include, for example, a thiol group. The second functional group may include, for example, a polymerizable vinyl group. The nanoparticles 14, 16 alternatively may be coated with other molecules, such as, for example, alkane thiol $HS(CH_2)_n$ chains with sulfur groups on one end, fluorophores, phosphate surfactants, and dendrimers. Many other molecules and functional groups are known in the art and can be used to coat the nanoparticles 14, 16. Furthermore, the spacer material 26 or precursor materials 26' may or may not be polymerizable.

A container 32, such as a commercially available Langmuir film trough, can be provided and filled with a fluid, such as water. Suitable Langmuir film troughs are sold by, for example, KSV Instruments of Helsinki, Finland. The coated nanoparticles 14, 16 can be dissolved in a solvent and dispersed on the surface of the fluid in the container 32 with, for example, a microsyringe. The organic solvent can be allowed to evaporate, leaving behind the coated nanoparticles 14, 16 on the surface of the fluid. If the coated particles 14, 16 are coated with spacer material 26 or precursor material 26' that include molecules having a hydrophobic portion thereof, the coated particles 14, 16 may form a floating monolayer 30 of nanoparticles 14, 16 on the surface of the fluid, as illustrated in FIG. 3. Such floating monolayers 30 are often referred to as Langmuir films. The container 32 can include a Wilhelmy plate electrobalance for measuring the surface pressure of the floating monolayer of nanoparticles 14, 16, and can also include movable barriers for reducing the surface area available to the floating monolayer 30 of nanoparticles 14, 16 on the surface of the fluid.

Figure 4:
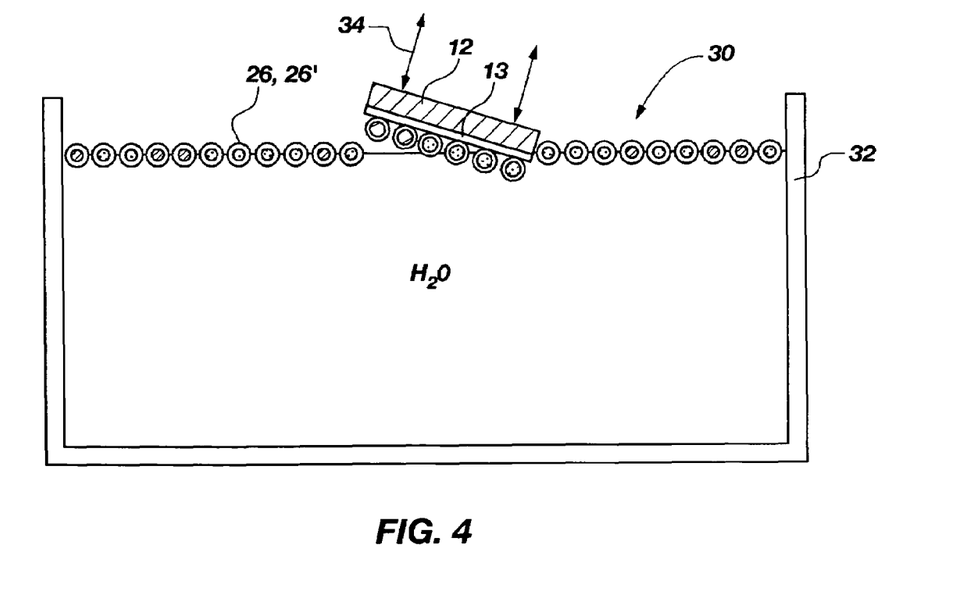

A substrate 12 can be provided and placed in contact with the monolayer 30 of coated nanoparticles 14, 16 (such as, e.g., by lowering substrate 12 into floating monolayer 30 as indicated by arrow 34), as shown in FIG. 4. This process transfers the floating monolayer of coated nanoparticles 14, 16 to the surface of the substrate 12, thereby forming a two-dimensional array of nanoparticles 14, 16 thereon. Alternatively, in another embodiment (not shown), a substrate 12 can be passed or pulled through the monolayer of coated nanoparticles 14, 16. In other words, the monolayer of coated nanoparticles 14, 16 may be transferred to the substrate 12 using either Langmuir Blodgett type techniques or Langmuir-Schaefer type techniques. Movable barriers can be used to compress the floating monolayer of inactive and active nanoparticles 14, 16 in the container 32 while the substrate is put in contact with the floating monolayer to control the ordering in the monolayer. The distance X (shown in FIG. 1) that separates nanoparticles 14, 16 from adjacent nanoparticles 14, 16 may be controlled by controlling the length or size of the molecules of the spacer material 26 or the precursor material 26' surrounding the nanoparticles 14, 16. In this manner, the spacer material 26 may be used to separate each nanoparticle 14, 16 in the array of nanoparticles from adjacent nanoparticles 14, 16 by a selected distance X.

As shown in FIG. 4, a layer of attachment material 13 may be provided on or formed on a surface of the substrate 12. The layer of attachment material 13 may be used to attach the nanoparticles 14, 16 to the substrate 12. For example, the layer of attachment material 13 may be formed by chemically functionalizing the surface of the substrate 12 with functional groups that will adhere to the molecules of the spacer material 26 or the precursor material 26'. For example, the surface of the substrate 12 may be functionalized by providing Si-O-H groups on a surface of the substrate 12. Alternatively, material that will adhere to, polymerize with, or otherwise chemically bind to the spacer material 26 or the precursor material 26' coating the nanoparticles 14, 16 may be deposited on a surface of the substrate 12 to form the layer of attachment material 13. In this manner, the layer of attachment material 13 may adhere to and immobilize the nanoparticles 14, 16 on a surface of the substrate 12. Furthermore, the layer of attachment material 13 may include the same material as the spacer material 26 or the precursor material 26'.

In one particular embodiment of the invention, the two-dimensional array of nanoparticles 14, 16 may be coated with a precursor material 26' that will be used to form the spacer material 26, and the coated nanoparticles 14, 16 may be provided on the surface of a fluid to form a Langmuir film. The precursor material 26' and the layer of attachment material 13 each may include polymerizable functional groups, which may be polymerized to stabilize the two-dimensional array of nanoparticles 14, 16 on the surface of the substrate 12. The precursor material 26' and the layer of attachment material 13 may be polymerized by processes specific to the polymerizable functional groups of the molecules of the precursor material 26' and the layer of attachment material 13.

Figure 5:
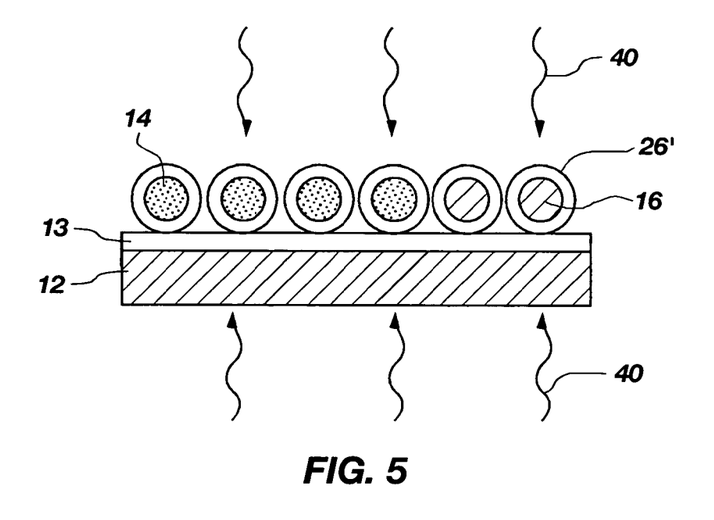
Figure 6:
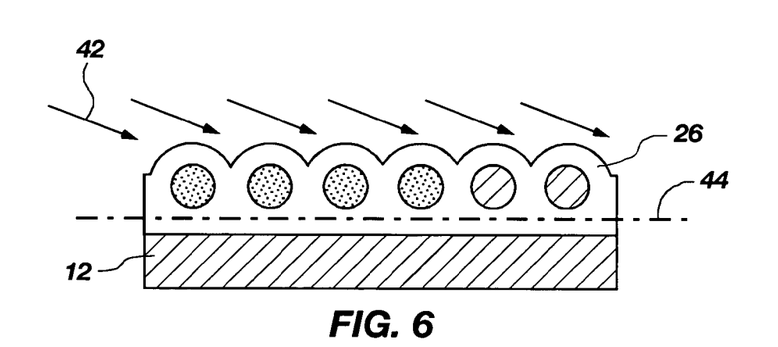

For example, the precursor material 26' and the layer of attachment material 13 may be subjected to radiation 40 (as illustrated in FIG. 5), which may cause the polymerizable functional groups of the spacer material 26 and the layer of attachment material 13 to polymerize and bind to adjacent molecules. As shown in FIG. 6, in this manner, a monolithic layer of spacer material 26 may be formed from the precursor material 26' coating each nanoparticle 14, 16 and the layer of attachment material 13. In FIG. 6, the portion of the spacer material 26 that has been formed primarily from the precursor material 26' is shown above the imaginary dividing line 44, while the portion of the spacer material 26 that has been formed primarily from the layer of attachment material 13 is shown below the imaginary dividing line 44. This monolithic layer of spacer material 26 may bind the nanoparticles 14, 16 to adjacent nanoparticles 14, 16 and to the substrate 12, thereby providing a solid, stable and durable structure for use as a NERS-active substrate.

If radiation 40 will be used to polymerize or cross-link the spacer material 26 and the layer of attachment material 13, the substrate 12 may be transparent to the particular wavelengths of radiation used to allow the radiation to impinge on the spacer material 26 and the layer of attachment material 13 through the bottom of the substrate 12. Alternatively, the spacer material 26 may include functional groups that can be bound by, for example, the addition of heat or by the addition of chemical reagents.

In another embodiment, the spacer material 26 may include thermoplastic material, which may be subjected to heat in order to at least partially melt the thermoplastic material coating each nanoparticle 14, 16. Upon cooling and re-solidification of the thermoplastic material, the thermoplastic material may stabilize the two-dimensional array of nanoparticles 14, 16 on the surface of the substrate 12.

A portion of the spacer material 26 can be removed to expose at least a portion of the surface of the nanoparticles 14, 16. The portion of the spacer material 26 can be removed by, for example, an ion milling process in which high energy ions 42 are directed onto the surface of the spacer material 26, as shown in FIG. 6. Alternatively, a portion of the spacer material 26 can be removed by, for example, a selective wet or dry (e.g., plasma) chemical etch that removes the spacer material 26 without reacting with or otherwise affecting the nanoparticles 14, 16. Such techniques are known in the art.

Figure 7:
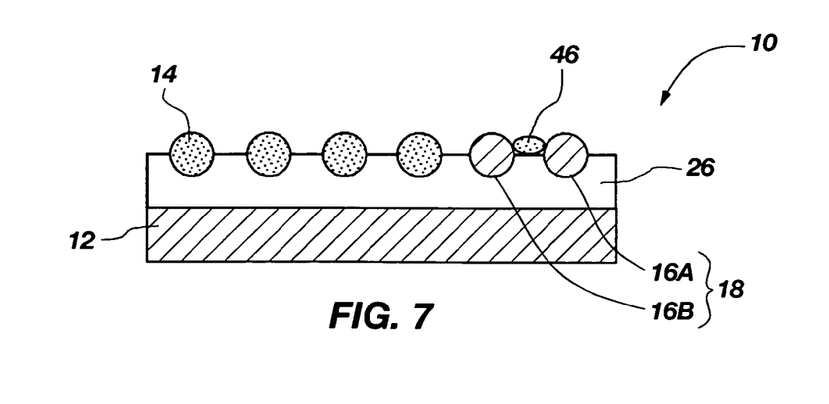

Removing a portion of the spacer material 26 produces the NERS-active structure 10 shown in FIG. 7. FIG. 7 is substantially similar to FIG. 2. However, an analyte 46 upon which it is desired to perform NERS is shown disposed in the region between a first metallic active nanoparticle 16A and a second metallic active nanoparticle 16B. The first metallic active nanoparticle 16A and the second metallic active nanoparticle 16B together form the isolated pair 18 of FIG. 1. When the NERS-active structure 10 is subjected to electromagnetic radiation having a frequency that corresponds to the plasmon resonance frequency exhibited by the metallic active nanoparticles 16, large gradients in the electric field can be produced at the region between the first active metallic nanoparticle 16A and the second active metallic nanoparticle 16B of isolated pair 18. These gradients have been shown to enhance the Raman scattering of photons by an analyte when the analyte is disposed in and subjected to these gradients in the electromagnetic fields. Similar gradients in the electric field also may be generated in the regions of isolated triplets such as triplet 20, isolated quadruplets such as quadruplet 22, etc.

NERS-active structures that embody teachings of the present invention such as the NERS-active structure 10 of FIGS. 1-2 can be used in NERS systems to perform NERS on an analyte. An exemplary NERS system 50 that embodies teachings of the present invention is illustrated schematically in FIG. 8. The NERS system 50 can include a NERS-active structure embodying teachings of the invention, such as, for example, the NERS-active structure 10 of FIGS. 1-2. The NERS system 50 can include a sample or analyte stage 52 for holding the NERS-active structure 10 and an analyte, an excitation radiation source 54 for providing excitation radiation 64, and a detector 56 for detecting Raman scattered radiation 66. The NERS system 50 can also include various optical components 60 such as, for example, lenses and filters positioned between the excitation radiation source 54 and the analyte stage 52 and between the analyte stage 52 and the detector 56.

Figure 8:
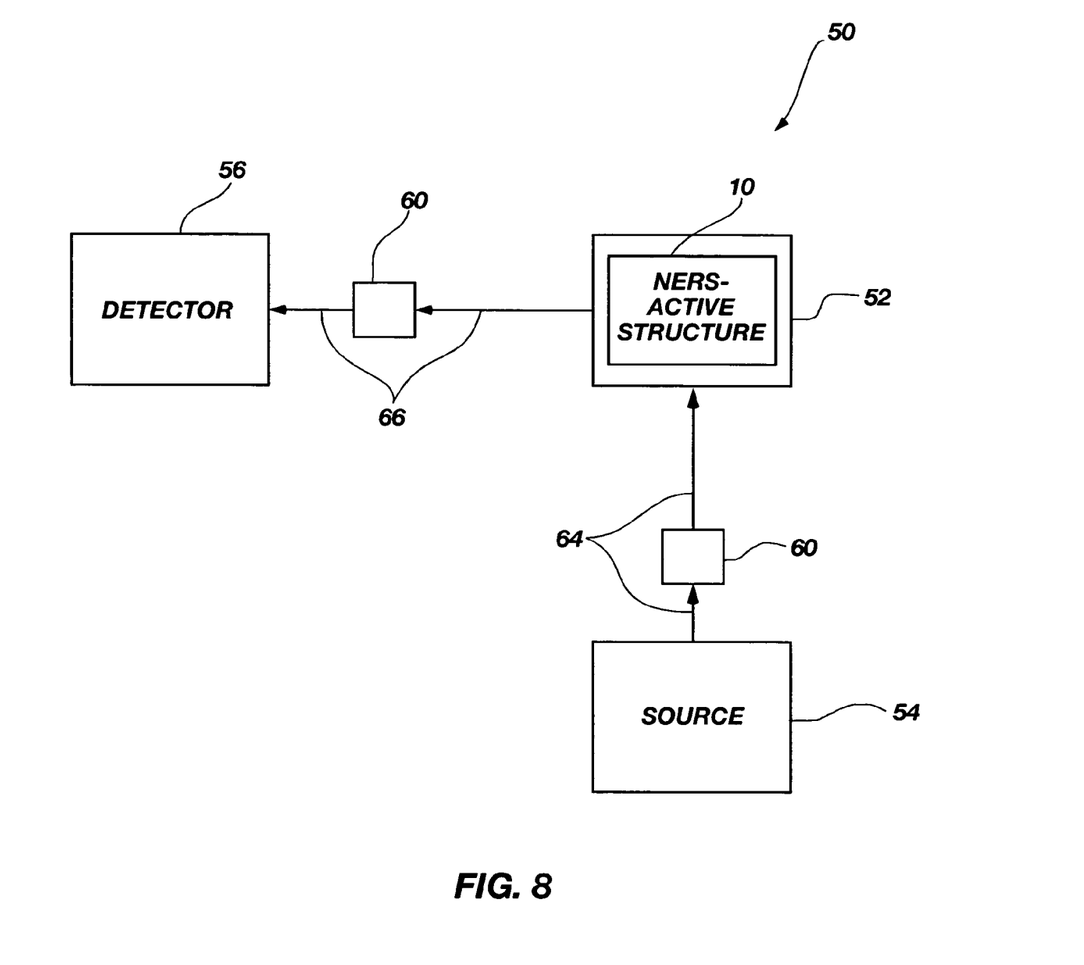
FIG. 8 is a schematic diagram of an exemplary NERS system for performing nano-enhanced Raman spectroscopy using a NERS-active structure according to the invention.

The excitation radiation source 54 can include any suitable source for emitting radiation at the desired wavelength, and can be capable of emitting a tunable wavelength of radiation. For example, commercially available semiconductor lasers, helium-neon lasers, carbon dioxide lasers, radiation-emitting diodes, incandescent lamps, and many other known radiation-emitting sources can be used as the excitation radiation source 54. The wavelengths that are emitted by the excitation radiation source 54 can include a suitable wavelength for performing NERS on the analyte. An exemplary range of wavelengths that can be emitted by the excitation radiation source 54 includes wavelengths between about 350 nanometers and about 1000 nanometers.

The detector 56 receives and detects the Raman scattered radiation 66 generated by Raman scattered photons that are scattered by the analyte. The detector 56 includes a device for determining the wavelength of the Raman scattered radiation 66 such as, for example, a monochromator, and a device for determining the intensity of the Raman scattered radiation 66 such as, for example, a photomultiplier. Typically, the Raman scattered radiation 66 is scattered in all directions relative to the analyte stage 52. Thus, the position of the detector 56 relative to the analyte stage 52 is not particularly important. However, the detector 56 can be positioned at, for example, an angle of 90° relative to the direction of the incident excitation radiation 64 to minimize the intensity of any excitation radiation 64 that is incident on the detector 56.

Optical components 60 positioned between the source 54 and the analyte stage 52 can be used to collimate, filter, or focus the excitation radiation 64 before the excitation radiation 54 impinges on the analyte stage 52 and the NERS-active structure 10. Optical components 60 positioned between the analyte stage 52 and the detector 56 can be used to collimate, filter, or focus the Raman scattered radiation 66. For example, a filter or a plurality of filters can be employed to prevent radiation at wavelengths corresponding to the excitation radiation 64 from impinging on the detector 56, thus allowing only the Raman scattered radiation 66 to be received by the detector 56.

To perform NERS using the NERS system 50, an analyte can be provided adjacent the NERS-active structure 10, and particularly adjacent the metallic active nanoparticles 16. The NERS-active structure 10 and the analyte are then irradiated with excitation radiation 64 provided by the source 54. Raman scattered radiation 66 scattered by the analyte is detected by the detector 56. The NERS-active structure 10 of the analyte stage 52 may enhance the intensity of the Raman scattered radiation that is scattered by the analyte as described previously herein.

The wavelengths and corresponding intensity of the Raman scattered radiation 66 can be determined and used to identify and provide information about the analyte.

The methods disclosed herein allow for the formation of NERS-active structures that include metallic active nanoparticles having well controlled size, spacing, and density. These structures allow for improved nano-enhanced Raman spectroscopy and can be employed as analyte substrates that can significantly enhance the intensity of Raman scattered radiation scattered by an analyte disposed adjacent thereto. The performance of nanoscale electronics, optoelectronics, molecular sensors, and other devices employing the Raman effect can be improved by using the NERS-active structures disclosed herein.

Although the foregoing description contains many specifics, these are not to be construed as limiting the scope of the present invention, but merely as providing certain exemplary embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A two-dimensional array of nanoparticles usable for enhancing Raman scattered radiation in NERS comprising:
   a first plurality of nanoparticles; and
   a second plurality of nanoparticles of size and shape substantially similar to the size and shape of the first plurality of nanoparticles, the second plurality of nanoparticles exhibiting a plasmon frequency differing from any plasmon frequency exhibited by the first plurality of nanoparticles, the second plurality of nanoparticles being interspersed among the first plurality of nanoparticles in the two-dimensional array of nanoparticles.

2. The two-dimensional array of nanoparticles as recited in claim 1, wherein the first plurality of nanoparticles and the second plurality of nanoparticles have a generally spherical shape and an average diameter of less than about 100 nanometers.

3. The two-dimensional array of nanoparticles as recited in claim 2, wherein the first plurality of nanoparticles and the second plurality of nanoparticles have an average diameter within a range from about 1 nanometer to about 25 nanometers.

4. The two-dimensional array of nanoparticles as recited in claim 1, wherein each nanoparticle in the two-dimensional array of nanoparticles is separated from adjacent nanoparticles in the two-dimensional array of nanoparticles by a distance in a range from about 1 nanometer to about 100 nanometers.

5. The two-dimensional array of nanoparticles as recited in claim 4, wherein each nanoparticle in the two-dimensional array of nanoparticles is separated from adjacent nanoparticles in the two-dimensional array of nanoparticles by a distance in a range from about 1 nanometer to about 50 nanometers.

6. The two-dimensional array of nanoparticles as recited in claim 5, wherein each nanoparticle in the two-dimensional array of nanoparticles is separated from adjacent nanoparticles in the two-dimensional array of nanoparticles by a distance in a range from about 1 nanometer to about 10 nanometers.

7. The two-dimensional array of nanoparticles as recited in claim 1, wherein the concentration of the second plurality of nanoparticles in the two-dimensional array of nanoparticles is below or near a percolation threshold.

8. The two-dimensional array of nanoparticles as recited in claim 1, wherein each nanoparticle of the second plurality of nanoparticles comprises one of gold, silver, and copper.

9. The two-dimensional array of nanoparticles as recited in claim 1, wherein each nanoparticle of the first plurality of nanoparticles comprises one of cobalt, silica, and alumina.

10. The two-dimensional array of nanoparticles as recited in claim 1, wherein the first plurality of nanoparticles and the second plurality of nanoparticles form a monolayer disposed on a surface of a substrate.

11. The two-dimensional array of nanoparticles as recited in claim 10, wherein the substrate comprises one of silicon, silica, zirconia, alumina, tin oxides, perovskite oxides, and metals.

12. The two-dimensional array of nanoparticles as recited in claim 1, further comprising a spacer material disposed on each nanoparticle in the array of nanoparticles.

13. The two-dimensional array of nanoparticles as recited in claim 12, wherein the spacer material separates each nanoparticle in the array of nanoparticles from adjacent nanoparticles by a selected distance.

14. The two-dimensional array of nanoparticles as recited in claim 12, wherein the spacer material comprises organic ligands.

15. The two-dimensional array of nanoparticles as recited in claim 12, wherein the spacer material comprises a polymerized material.

16. The two-dimensional array of nanoparticles as recited in claim 12, wherein the spacer material covers less than the entire surface area of each nanoparticle in the two-dimensional array of nanoparticles.

17. A monolayer of nanoparticles for use as a NERS-active structure comprising:
   a first plurality of nanoparticles; and
   a second plurality of nanoparticles interspersed among the first plurality of nanoparticles in the monolayer of nanoparticles, the second plurality of nanoparticles exhibiting a plasmon frequency differing from any plasmon frequency exhibited by the first plurality of nanoparticles, the concentration of the second plurality of nanoparticles in the monolayer of nanoparticles being below or near a percolation threshold.

18. The monolayer of nanoparticles as recited in claim 17, wherein the first plurality of nanoparticles have a generally spherical shape and an average diameter of less than about 100 nanometers, and the second plurality of nanoparticles have a generally spherical shape and an average diameter substantially similar to the average diameter of the first plurality of nanoparticles.

19. The monolayer of nanoparticles as recited in claim 18, wherein the first plurality of nanoparticles and the second plurality of nanoparticles have an average diameter within a range from about 1 nanometer to about 25 nanometers.

20. The monolayer of nanoparticles as recited in claim 17, wherein the second plurality of nanoparticles comprise one of gold, silver, and copper.

21. The monolayer of nanoparticles as recited in claim 17, wherein the nanoparticles of the first plurality of nanoparticles comprise one of cobalt, silica, and alumina.

22. The monolayer of nanoparticles as recited in claim 17, wherein the first plurality of nanoparticles and the second plurality of nanoparticles are disposed on a surface of a substrate.

23. The monolayer of nanoparticles as recited in claim 17, wherein the substrate comprises one of silicon, silica, zirconia, alumina, tin oxides, perovskite oxides, and metals.

24. The monolayer of nanoparticles as recited in claim 17, further comprising a spacer material disposed on each nanoparticle in the monolayer of nanoparticles.

25. The monolayer of nanoparticles as recited in claim 24, wherein the spacer material separates each nanoparticle in the array of nanoparticles from adjacent nanoparticles.

26. The monolayer of nanoparticles as recited in claim 25, wherein the spacer material comprises a polymerized material.

27. A NERS-active structure comprising:
   a substrate;
   a monolayer of nanoparticles disposed on a surface of the substrate comprising:
      a first plurality of nanoparticles; and
      a second plurality of nanoparticles interspersed among the first plurality of nanoparticles in the monolayer of nanoparticles, the second plurality of nanoparticles exhibiting a plasmon frequency differing from any plasmon frequency exhibited by the first plurality of nanoparticles, the concentration of the second plurality of nanoparticles in the monolayer of nanoparticles being below or near a percolation threshold; and a spacer material partially surrounding each nanoparticle in the monolayer of nanoparticles, the spacer material separating each nanoparticle from adjacent nanoparticles by a selected distance, the spacer material covering less than the entire surface area of each nanoparticle.

28. The NERS-active structure as recited in claim 27, wherein the first plurality of nanoparticles have a generally spherical shape and an average diameter within a range from about 1 nanometer to about 25 nanometers, and the second plurality of nanoparticles have a generally spherical shape and an average diameter substantially similar to the average diameter of the first plurality of nanoparticles.

29. The NERS-active structure as recited in claim 28, wherein the second plurality of nanoparticles comprise one of gold, silver, and copper.

30. The NERS-active structure as recited in claim 29, wherein the first plurality of nanoparticles comprise one of cobalt, silica, and alumina.

31. The NERS-active structure as recited in claim 27, wherein each nanoparticle in the monolayer of nanoparticles is separated from adjacent nanoparticles in the monolayer of nanoparticles by a distance in a range from about 1 nanometer to about 50 nanometers.

32. The NERS-active structure as recited in claim 31, wherein each nanoparticle in the monolayer of nanoparticles is separated from adjacent nanoparticles in the monolayer of nanoparticles by a distance in a range from about 1 nanometer to about 10 nanometers.

33. The NERS-active structure as recited in claim 27, wherein the spacer material comprises a polymerized material.

34. The NERS-active structure as recited in claim 27, wherein the spacer material comprises organic ligands.

35. The NERS-active structure as recited in claim 27, further comprising a layer of attachment material disposed on a surface of the substrate, the layer of attachment material being configured to adhere to the spacer material partially surrounding each nanoparticle in the monolayer of nanoparticles.

36. The NERS-active structure as recited in claim 27, wherein a surface of the substrate is functionalized to adhere to the spacer material partially surrounding each nanoparticle in the monolayer of nanoparticles.

37. A method for forming a NERS-active structure comprising:

providing a mixture of nanoparticles, the mixture comprising a first plurality of nanoparticles comprising a first material and a second plurality of nanoparticles comprising a second material, the concentration of the second plurality of nanoparticles in the mixture being less than the concentration of the first plurality of nanoparticles, the second plurality of nanoparticles exhibiting a plasmon frequency differing from any plasmon frequency exhibited by the first plurality of nanoparticles;

coating each nanoparticle in the mixture of nanoparticles with a spacer material;

forming a monolayer of the nanoparticles on a surface of a fluid;

providing a substrate;

transferring the monolayer of nanoparticles from the surface of the fluid to a surface of the substrate by placing the substrate in contact with the monolayer of nanoparticles on the surface of the fluid; and removing at least a portion of the spacer material.

38. The method for forming a NERS-active structure as recited in claim 37, wherein removing at least a portion of the spacer material comprises ion milling a portion of the spacer material from a portion of the surface of each nanoparticle.

39. The method for forming a NERS-active structure as recited in claim 37, wherein providing a mixture of nanoparticles comprises providing a mixture having a first plurality of nanoparticles formed from a first material and a second plurality of nanoparticles formed from a second material, the concentration of the second plurality of nanoparticles in the mixture being below or near a percolation threshold when the nanoparticles are disposed in a monolayer.

40. The method for forming a NERS-active structure as recited in claim 37, wherein coating each nanoparticle in the mixture of nanoparticles with spacer material comprises coating each nanoparticle in the mixture of nanoparticles with a polymerizable material.

41. The method for forming a NERS-active structure as recited in claim 40, further comprising polymerizing the polymerizable material.

42. The method for forming a NERS-active structure as recited in claim 37, wherein coating each nanoparticle in the mixture of nanoparticles with spacer material comprises coating each nanoparticle in the mixture of nanoparticles with organic ligands.

43. The method for forming a NERS-active structure as recited in claim 37, further comprising providing a layer of attachment material on a surface of the substrate, the layer of attachment material being configured to adhere to the spacer material.

44. The method for forming a NERS-active structure as recited in claim 43, wherein providing a layer of attachment material on a surface of the substrate comprises functionalizing a surface of the substrate to promote adherence of the nanoparticles to the substrate.

45. A NERS system comprising:

a NERS-active structure comprising a monolayer of nanoparticles, the monolayer comprising:

a first plurality of nanoparticles; and a second plurality of nanoparticles interspersed among the first plurality of nanoparticles in the monolayer of nanoparticles, the second plurality of nanoparticles exhibiting a plasmon frequency differing from any plasmon frequency exhibited by the first plurality of nanoparticles, the concentration of the second plurality of nanoparticles in the monolayer of nanoparticles being below or near a percolation threshold;

an excitation radiation source configured to irradiate the NERS-active structure; and a detector configured to detect Raman scattered radiation scattered by an analyte located adjacent the NERS-active structure.

46. The NERS system as recited in claim 45, wherein the first plurality of nanoparticles have a generally spherical shape and an average diameter within a range from about 1 nanometer to about 25 nanometers, and the second plurality of nanoparticles have a generally spherical shape and an average diameter substantially similar to the average diameter of the first plurality of nanoparticles.

47. The NERS system as recited in claim 46, wherein the first plurality of nanoparticles and the second plurality of nanoparticles have an average diameter within a range from about 1 nanometer to about 25 nanometers.

48. The NERS system as recited in claim 45, wherein the second plurality of nanoparticles comprise one of gold, silver, and copper.

49. The NERS system as recited in claim 48, wherein the first plurality of nanoparticles comprise one of cobalt, silica, and alumina.

50. The NERS system as recited in claim 45, wherein each nanoparticle in the monolayer of nanoparticles is separated from adjacent nanoparticles by a spacer material, the spacer material covering less than the entire surface area of each nanoparticle in the monolayer of nanoparticles.

* * * * *